(12) United States Patent
Rootes et al.

(10) Patent No.: US 12,208,175 B2
(45) Date of Patent: Jan. 28, 2025

(54) DISPOSABLE CLEANING UNITS FOR A REUSABLE MEDICAL DEVICE

(71) Applicant: Covidien LP, Mansfield, MA (US)

(72) Inventors: Matthew A. Rootes, Crystal, MN (US); Nathan J. Knutson, Long Lake, MN (US)

(73) Assignee: Covidien LP, Mansfield, MA (US)

( * ) Notice: Subject to any disclaimer, the term of this patent is extended or adjusted under 35 U.S.C. 154(b) by 316 days.

(21) Appl. No.: 17/824,258

(22) Filed: May 25, 2022

(65) Prior Publication Data

US 2022/0378965 A1 Dec. 1, 2022

Related U.S. Application Data

(60) Provisional application No. 63/193,026, filed on May 25, 2021.

(51) Int. Cl.
| | | |
|---|---|---|
| A61L 2/18 | (2006.01) | |
| A61L 2/24 | (2006.01) | |
| A61L 2/26 | (2006.01) | |
| B08B 9/027 | (2006.01) | |
| B08B 9/032 | (2006.01) | |
| B08B 9/04 | (2006.01) | |

(52) U.S. Cl.
CPC ................... *A61L 2/26* (2013.01); *A61L 2/18* (2013.01); *A61L 2/24* (2013.01); *B08B 9/027* (2013.01); *B08B 9/032* (2013.01); *B08B 9/04* (2013.01); *A61L 2202/122* (2013.01); *A61L 2202/15* (2013.01); *A61L 2202/17* (2013.01); *A61L 2202/24* (2013.01)

(58) Field of Classification Search
None
See application file for complete search history.

(56) References Cited

U.S. PATENT DOCUMENTS

| | | |
|---|---|---|
| 4,278,101 A | 7/1981 | Tanaka et al. |
| 4,281,674 A | 8/1981 | Tanaka et al. |
| 4,288,882 A | 9/1981 | Takeuchi |
| 4,391,287 A | 7/1983 | Konoshima |
| 4,525,220 A | 6/1985 | Sasa et al. |
| 4,526,622 A | 7/1985 | Takamura et al. |
| 4,526,623 A | 7/1985 | Ishii et al. |
| 4,537,209 A | 8/1985 | Sasa |
| 4,576,650 A | 3/1986 | Yabe et al. |
| 4,579,597 A | 4/1986 | Sasa et al. |
| 4,579,598 A | 4/1986 | Sasa et al. |
| 4,637,378 A | 1/1987 | Sasa |
| 4,667,691 A | 5/1987 | Sasa |
| 5,240,675 A | 8/1993 | Wilk et al. |
| 5,297,537 A | 3/1994 | Savitt et al. |
| 5,408,991 A | 4/1995 | Iida et al. |
| 5,494,637 A | 2/1996 | Barlow |
| 5,630,795 A | 5/1997 | Kuramoto et al. |
| 6,379,632 B1 | 4/2002 | Kinoshita et al. |

(Continued)

FOREIGN PATENT DOCUMENTS

| | | |
|---|---|---|
| EP | 2253264 A1 | 11/2010 |
| WO | 2000056203 A1 | 9/2000 |

*Primary Examiner* — Levon J Shahinian
(74) *Attorney, Agent, or Firm* — Weber Rosselli & Cannon LLP (57) ABSTRACT

A disposable cleaning unit is described herein including an inner receptacle and an outer receptacle.

15 Claims, 10 Drawing Sheets

(56) References Cited

U.S. PATENT DOCUMENTS

| | | |
|---|---|---|
| 6,582,654 B1 | 6/2003 | Kral et al. |
| 7,608,229 B2 | 10/2009 | Kotani et al. |
| 7,648,023 B2 | 1/2010 | Maguire, Jr. et al. |
| 7,758,704 B2 | 7/2010 | Hasegawa et al. |
| 8,034,193 B2 | 10/2011 | Suzuki et al. |
| 8,226,774 B2 | 7/2012 | Labib et al. |
| 8,256,057 B2 | 9/2012 | Galantai et al. |
| 8,298,494 B2 | 10/2012 | Komiya et al. |
| 8,366,834 B2 | 2/2013 | Komiya et al. |
| 8,444,930 B2 | 5/2013 | Komiya et al. |
| 8,566,995 B2 | 10/2013 | Asano et al. |
| 8,715,425 B2 | 5/2014 | Sewake et al. |
| 8,840,733 B2 | 9/2014 | Komiya et al. |
| 8,858,731 B2 | 10/2014 | Komiya et al. |
| 9,027,574 B2 | 5/2015 | Kosugi et al. |
| 9,204,936 B2 | 12/2015 | Kawachi |
| 9,233,181 B2 | 1/2016 | Komiya et al. |
| 9,414,742 B2 | 8/2016 | Sato |
| 9,420,942 B2 | 8/2016 | Taya |
| 9,462,935 B2 | 10/2016 | Takazawa et al. |
| 9,505,038 B2 | 11/2016 | Iwasaki |
| 9,603,513 B2 | 3/2017 | Takada et al. |
| 9,610,008 B2 | 4/2017 | Kawachi |
| 9,636,006 B2 | 5/2017 | Kogure |
| 9,730,577 B2 | 8/2017 | Komiya et al. |
| 9,872,603 B2 | 1/2018 | Sato et al. |
| 9,907,460 B2 | 3/2018 | Patzek, IV |
| 10,448,818 B2 | 10/2019 | Komiya et al. |
| 10,835,114 B2 | 11/2020 | King et al. |
| 2007/0234495 A1 | 10/2007 | Suzuki et al. |
| 2007/0251039 A1 | 11/2007 | Kobayashi et al. |
| 2008/0251102 A1 | 10/2008 | Haack et al. |
| 2010/0139018 A1 | 6/2010 | Maslanka |
| 2016/0309989 A1* | 10/2016 | Sato .................. A61B 1/12 |
| 2017/0296046 A1* | 10/2017 | King .................. B08B 9/0321 |

* cited by examiner

DISPOSABLE CLEANING UNITS FOR A REUSABLE MEDICAL DEVICE

CROSS-REFERENCE TO RELATED APPLICATION

This application claims the benefit of and priority to U.S. Provisional Patent Application No. 63/193,026 filed on May 25, 2021, the entire disclosure of each of which is incorporated by reference herein.

BACKGROUND

Technical Field

The present disclosure is generally related to disposable cleaning units, and more particularly, disposable cleaning units configured for cleaning a working channel of a reusable medical device.

Description of Related Art

Reusable medical devices including a working channel defined therein are currently being cleaned or re-cleaned in hospital-owned facilities wherein ovens, irradiation, high pressure, chemicals, etc. are used to ensure the medical devices are properly cleaned and suitable for reuse and/or multiple use. Reusable medical devices may also further include highly sensitive, technical, and costly internal components which are necessary for the device to properly operate but are not typically in need of cleaning and/or re-cleaning because these components are internal only and not routinely exposed to contaminants. However, each time the medical device is cleaned or re-cleaned as a whole, these internal components are still exposed to the high temperatures, high pressure and/or radiation used to clean the entire device including the internal working channel defined therein. Although this global exposure cleans the working channel defined within the medical device, the repeated global exposure of the entire device can cause damage to the more sensitive technical and highly costly internal components over time. Thus, there exists a need to clean and/or re-clean a working channel defined within the medical device in a more localized manner which reduces global exposure to the entire device (including the internal technical components) and which can be done cheaply, quickly, and on an individual, disposable basis.

SUMMARY

The present disclosure describes disposable single-use cleaning units for reusable medical devices including at least one working channel defined therethrough. The cleaning units include an inner receptacle and an outer receptacle. In some embodiments, the inner receptacle is sealable and/or configured to be sealed. In some embodiments, the outer receptacle is sealable and/or configured to be sealed.

In some embodiments, the inner receptacle includes a first cavity, a first inner tubular connector, and a second inner tubular connector. The first cavity is configured to receive a reusable medical device therein. The reusable medical device includes a working channel defined therethrough. The working channel extends between a first opening and a second opening on the reusable medical device.

The first inner tubular connector defines a first inner channel extending between a first receptacle port and a first device port. The second inner tubular connector defines a second inner channel extending between a second receptacle port and a second device port. The first and second device ports are configured to connect to and/or fluidly communicate with the first and second openings, respectively, of the working channel of the reusable medical device.

In some embodiments, the outer receptacle includes a first chamber and a second chamber, a first and second reservoir, and a first and second outer tubular connector. The first chamber being configured to receive the inner receptacle therein, with or without the medical device. The second chamber includes at least a portion of an actuator positioned therein and connected to a second cleaning device portion of the cleaning device.

The first reservoir is configured to store a cleaning fluid and the second reservoir is configured to store at least a first cleaning device portion of the cleaning device. The first and second reservoirs are separated by a frangible member. In some embodiments, both the first and second reservoirs are located within the first chamber.

The first outer tubular connector defines a first outer channel extending between a first base end attached to the second reservoir and a first outer port. The first outer port is configured to connect to and/or fluidly communicate with the first receptacle port of the first inner tubular connector when attached thereto, without leaking. The second outer tubular connector defines a second outer channel extending between a second base end attached to the second chamber and a second outer port. The second outer port is configured to connect to and/or fluidly communicate with the second receptacle port of the second inner tubular connector when attached thereto, without leaking.

In some embodiments, the reusable medical device is an endoscope. In some embodiments, the reusable medical device includes a bronchoscope.

In some embodiments, the inner receptacle is a thermoform and the outer receptacle is a sealable pouch.

Methods of cleaning a reusable medical device including a working channel defined therethrough are also provided herein.

BRIEF DESCRIPTION OF THE DRAWINGS

Various embodiments are described herein by way of example in conjunction with the following.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present disclosure is directed in part to disposable cleaning units for medical devices designed to be reused and/or recycled after cleaning. The cleaning units described herein are configured to clean one or more working channels defined within the medical device which may become contaminated with various surgical debris (e.g., various bodily fluids, tissue, bacteria, and the like) after use.

The cleaning units described herein include at least one disposable inner receptacle and at least one disposable outer receptacle. The inner receptacle is configured to receive and/or maintain the reusable medical device therein. The outer receptacle is configured to receive and/or maintain the inner receptacle therein, with or without the reusable medical device.

Figure 1:
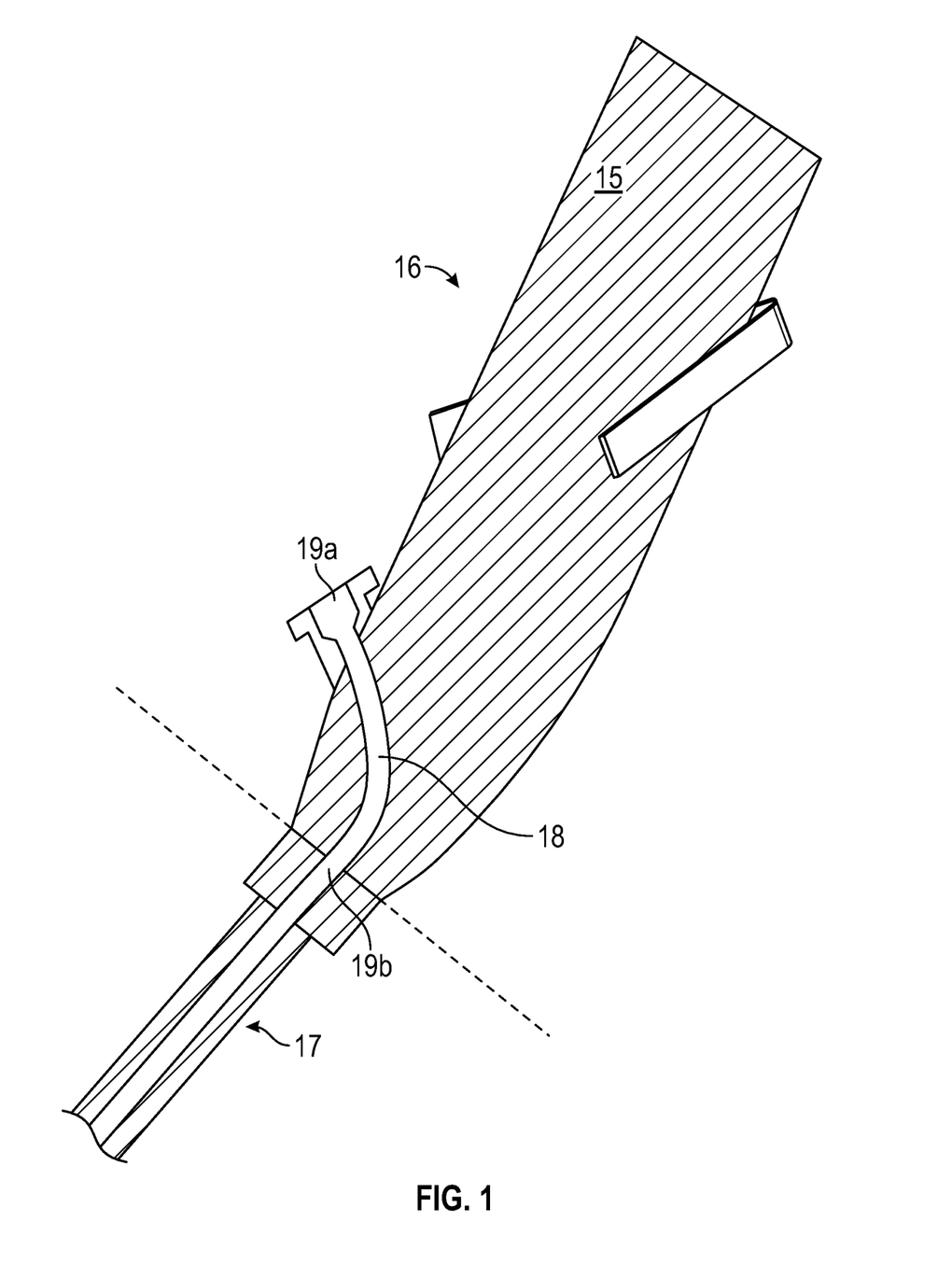
FIG. 1 is a schematic cross-sectional side view of a reusable medical device as described in at least one embodiment herein.

FIG. 1 depicts a schematic cross-section of a reusable medical device 15, such as an endoscope or bronchoscope, as described herein including a handle 16 on a proximal end thereof and a removable and/or disposable shaft 17 extending in a distal direction from the handle 16. The reusable medical device 15, and particularly the handle 16, includes one or more working channels 18 defined therethrough. Each working channel 18 extending between a first channel opening 19a and a second channel opening 19b opposite the first channel opening 19a. The shaft 16 is shown attached to and extending distally from the device 15 but is configured to be removably connected thereto, such as a removable and/or disposable shaft, prior to cleaning of the reusable medical device 15.

The cleaning units described herein may be configured to clean any reusable medical device including at least one working channel defined therethrough. In some embodiments, the medical device is an endoscope. Some non-limiting examples of suitable endoscopes include gastroscopes, colonoscopes, bronchoscopes, laryngoscopes, cytoscopes, hysteroscopes, and ureteroscopes. In some embodiments, the reusable medical device is a bronchoscope and particularly the handle portion of the bronchoscope.

Figure 2:
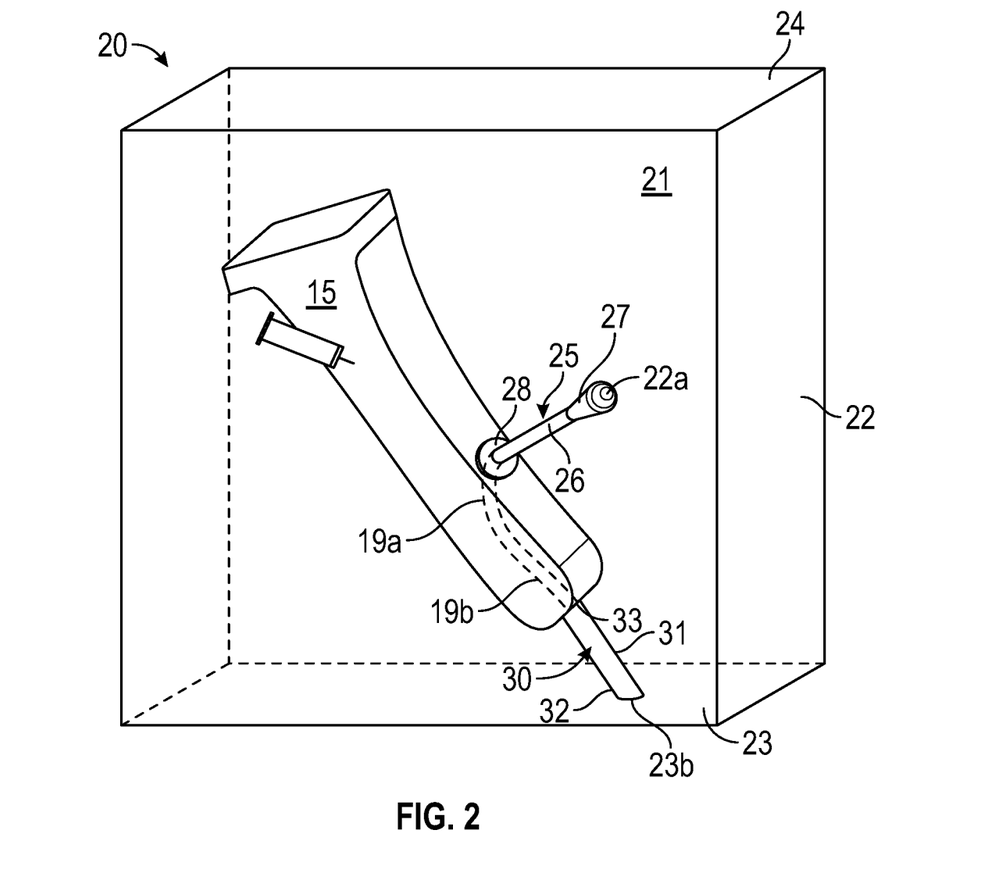
FIG. 2 is a schematic perspective view of an inner receptacle of a disposable cleaning unit as described in at least one embodiment herein.

FIG. 2 depicts the reusable medical device 15, such as an endoscope or bronchoscope, positioned within a first cavity 21 defined by an inner receptacle 20. The inner receptacle 20 includes at least a first inner tubular connector 25 and a second inner tubular connector 30 configured to connect to and/or form fluid communication with the first and second channel openings 19a, 19b, respectively. The first inner tubular connector 25 defines a first inner channel 26 extending between a first receptacle port 27 and a first device port 28. As shown in FIG. 2, the first device port 28 is connected to the first opening 19a in a manner in which fluid, such as a cleaning fluid, may be communicated and/or passed therethrough without leaking.

The second inner tubular connector 30 defines a second inner channel 31 extending between a second receptacle port 32 and a second device port 33. As further shown in FIG. 2, the second device port 33 is connected to the second opening 19b in a manner in which fluid, such as a cleaning fluid, may be communicated and/or passed therethrough without leaking.

As further shown in FIG. 2, in some embodiments, the inner receptacle 20 may include one or more side walls 22 extending from a base wall 23 defining the first cavity 21. In some embodiments, the inner receptacle 20 may include a cover 24 positioned on the side wall(s) 21 opposite the base wall 23, thereby creating a closed first cavity 21. In some embodiments, the inner receptacle may not include a cover thereby creating an open first cavity.

As further depicted in FIG. 2, at least a portion of the first tubular connector 25 is defined and/or maintained within a first wall portion 22a of sidewall 22. In some embodiments, the first receptacle port 27 is defined and/or maintained with the first wall portion 22a of the at least one sidewall 22 while the first device port 28 and at least a majority of the first inner channel 26 extend from the at least one sidewall into the first cavity 21 providing the flexibility to move and/or adjust the location of the first device port 28 and/or the first inner channel 26 for efficient attachment to the first opening 19a. In some embodiments, at least a majority of, if not the entire, first inner tubular connector 25 is defined and/or maintained within a first wall portion 22a of sidewall 22.

As still further depicted in FIG. 2, at least a portion of the second tubular connector 30 is defined and/or maintained within a second wall portion 23b of the base wall 23. It is envisioned however that in some embodiments, the second wall portion 23b may be defined within the at least one side wall 22 at a location closer to the base wall 23 than the first wall portion 22a.

In some embodiments, the second receptacle port 32 is defined and/or maintained with the second wall portion 23b while the second device port 33 and at least a majority of the second inner channel 31 extend from the second wall portion 23b and/or base wall 23 into the first cavity 21 providing the flexibility to move and/or adjust the location of the second device port 33 and/or the second inner channel 31 for efficient attachment to the second opening 19b. In some embodiments, at least a majority of, if not the entire, second inner tubular connector 30 is defined and/or maintained within the second wall portion 23b of base wall 23.

In some embodiments, the first cavity 21, as shown in FIG. 2, is simply an open area defined by the shape of the inner receptacle in which the medical device 15 may be received and/or maintained for cleaning, however the medical device 15 is free to move or be positioned in any manner inside the first cavity 21. In still other embodiments, the first cavity may be molded to a predetermined shape configured to receive a specific type of medical device, such as an endoscope or bronchoscope, in a manner which locks the medical device into a non-movable position inside the first cavity.

The inner receptacle may be made from any suitable plastic and/or polymeric material and may be made using any suitable method. In some embodiments, the inner receptacle is formed using a thermosetting process to form a thermoform inner receptacle. Such thermosetting processes may include injection molding, extrusion molding, compression molding or spin casting. Some non-limiting examples of suitable materials include thermosetting polymers or plastics including acrylic resins, polyurethanes, vulcanized rubber, silicones, vinyl esters, and the like.

As further shown in FIG. 2, the first and second device ports 28, 33 of the inner tubular connectors 25, 30 are configured to connect and/or fluidly communicate with the openings 19a, 19b of the working channel 18. In addition, as described in more detail hereinbelow, the first and second receptacle ports 27, 32 are configured to connect and/or fluidly communicate with the first and second outer ports 58, 63 of the outer tubular connectors 55, 60 (FIGS. 6A-6D).

Figure 3A:
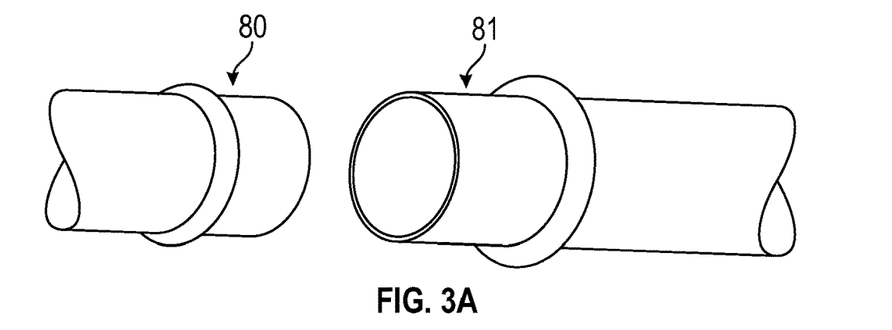
FIGS. 3A-3D are schematic side views of various ports and/or openings descried in at least one embodiment herein.
Figure 3B:
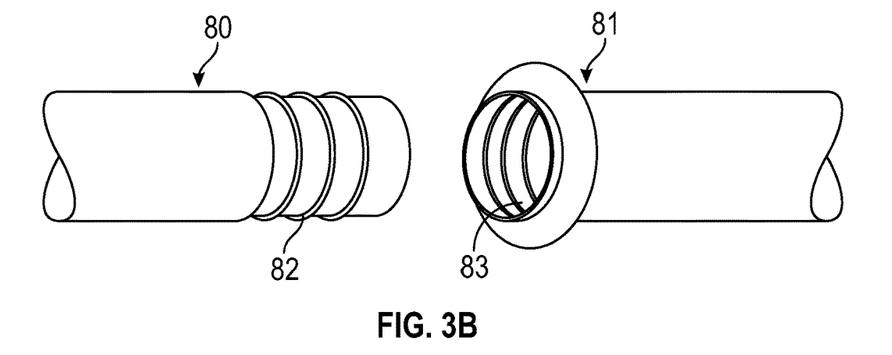
Figure 3C:
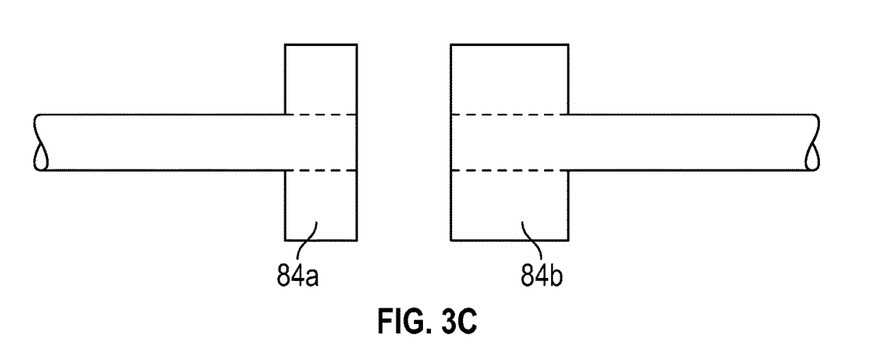
Figure 3D:
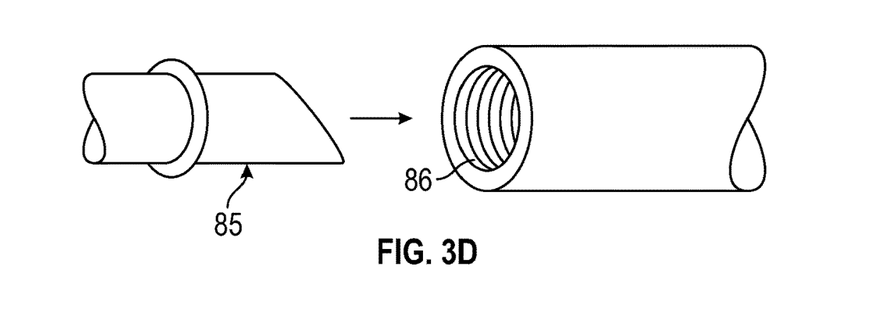

As shown in FIGS. 3A-3C, the various ports (and/or openings) are designed to be complimentary in that the two ports (and/or one port and one opening) are configured to connect to each other in a manner which is not easily separatable and does not allow for leaking of fluids. In some embodiments, as shown in FIGS. 3A and 3B, two complimentary ports (and/or one port and one opening which are complimentary) may include a male portion 80 and female portion 81 configured to matingly engage each other when connected and/or in fluid communication. As further shown in FIG. 3B, in some embodiments, at least one of the male or female portion 80, 81 may further include threads 82 and the other portion may include complimentary grooves 83 configured to receive the threads 82, thereby temporarily locking the male/female portions 80, 81 to each other. In still other embodiments, as shown in FIG. 3C, the various complimentary ports and openings described herein may include complimentary magnets 84a, 84b of opposite polarity which naturally attract each other when placed near or in direct contact with each other. In such embodiments, the ports and/or openings may or may not be of the male/female design. In still other embodiments, as shown in FIG. 3D, the various ports and/or openings may include a first piercing portion 85 configured to create an opening in a second pierceable portion 86, such as a rubber septum, when forced therethrough. The piercing portion including a beveled or sharpened edge suitable to create an opening through the pierceable portion 86.

Figure 4:
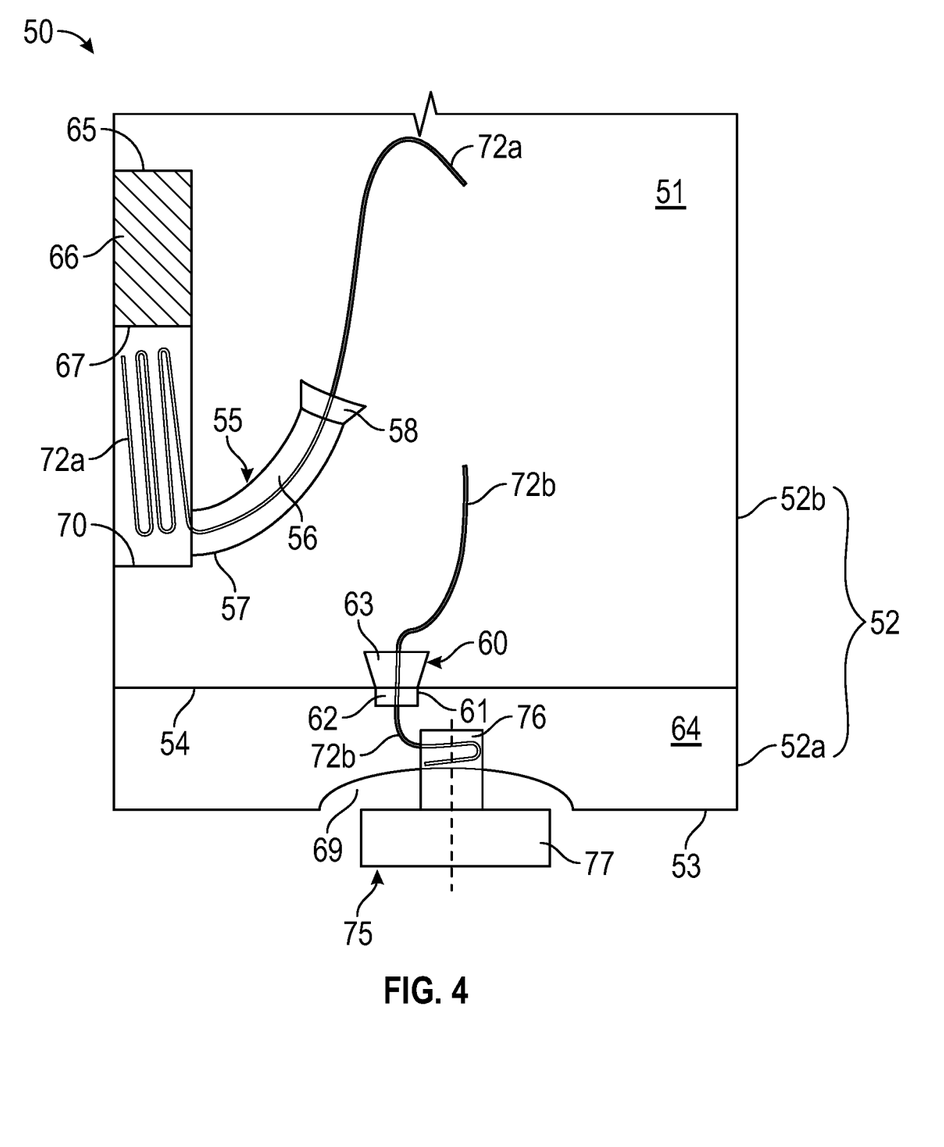
FIG. 4 is a schematic side view of an outer receptacle of a disposable cleaning unit as described in at least one embodiment herein.

Turning now to FIG. 4, which depicts a schematic cross-sectional view of the outer receptacle 50 including a first chamber 51 configured to receive and/or maintain the inner receptacle described herein, with or without the medical device, and a second chamber 64 separately sealed from the first chamber.

As further shown in FIG. 4, in some embodiments, the first and second chambers 51, 64 of the outer receptacle 50 may include one or more outer side walls 52 extending from an outer base wall 53 and a supplemental inner base wall 54 spaced from the outer base wall 53. The second chamber 64 being defined between a lower portion 52a of the one or more outer sidewalls 52 extending away from the outer base wall 53 and between the outer base wall 53 and the supplemental inner base wall 54. The first chamber 51 being defined by an upper portion 52b of the one or more side walls 52 extending from the supplemental inner base wall 54 in a direction opposite the outer base wall 53.

Figure 5A:
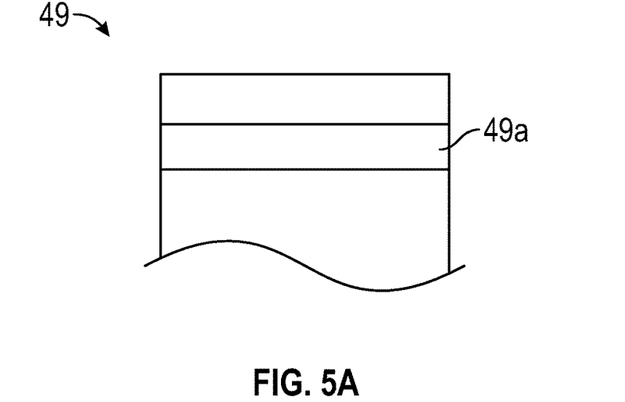
FIGS. 5A-5C are schematic side views of a top portion of the outer receptacle described in at least one embodiment herein.
Figure 5B:
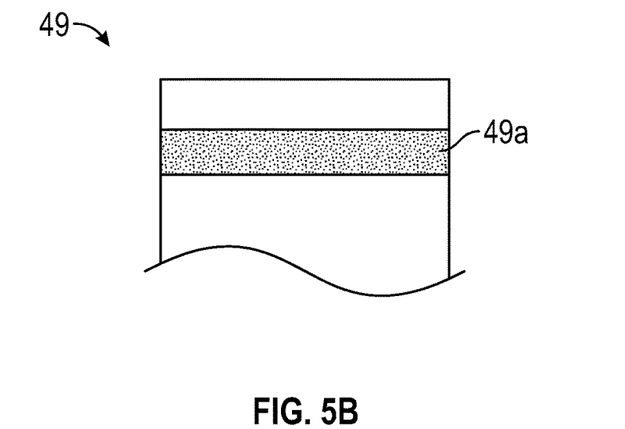
Figure 5C:
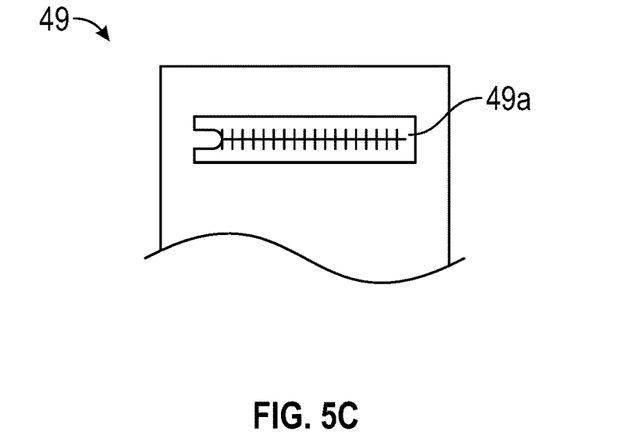

Although not depicted in FIG. 4, the first chamber 51 includes a sealable top portion 49 opposite the base walls 53, 54 configured to close and seal the first chamber 51 and/or the outer receptacle 50. As shown in FIGS. 5A-5C, the sealable top portion 49 may be configured to include any suitable resealable structure including but not limited to include a Zip-loc-type resealable structure (FIG. 5A), a hook-and-loop resealable structure (FIG. 5B), or a zipper-like resealable structure (FIG. 5C). The top portion also being configured to be folded or rolled.

As further shown in FIG. 4, the first chamber 51 includes a first reservoir 65 configured to store a cleaning fluid 66 therein, a second reservoir 70 configured to store a first cleaning device portion 72a of a cleaning device therein, and a frangible member 67 positioned between the first and second reservoirs 65, 70 separating the cleaning fluid 66 from the first cleaning device portion 72a. In some embodiments, the first cleaning device portion 72a is configured in a rolled or coiled orientation while maintained within the second reservoir 70. Please note, cleaning fluid 66 is schematically indicated with parallel lines to better illustrate the relationship between the cleaning fluid and the other parts of the cleaning unit, however the lines are not intended to represent any particular aspect of the clean fluid, e.g., particulate matter, viscosity, etc.

Any suitable cleaning fluid may be used for cleaning and/or disinfecting the working channel of the medical device. Some non-limiting examples include, but are not intended to be limited to, antiseptic liquids, antimicrobial liquids, antiviral liquids, sterile water, sterile saline, liquid detergents, and the like.

The frangible member may be made of any of a wide variety of materials with the only requirements being that the material not degrade due to contact with the cleaning fluid of the first reservoir. By frangible, the member is configured to be ruptured or broken when direct pressure is applied thereto with the intent to separate the frangible member into at least two separate pieces. An ideal frangible member is configured to not rupture or break prior to intended use, i.e., during manufacturing, sterilization, storage and/or transportation, but remains configured to be broken or ruptured when sufficient pressure is applied by the medical staff's hands.

The first reservoir 65 is shown positioned on top of the second reservoir 70 with the frangible member 67 positioned therebetween to try and ensure gravity will force the cleaning fluid 66 to exit the first reservoir 65 and enter the second reservoir 70 following the rupture of the frangible member 67. In some embodiments, the first and second reservoirs 65, 70 are stacked on top of each other along the top portion 52b of the side wall 52 inside the first chamber 51.

As further depicted in FIG. 4, the first chamber 51 also includes first and second outer tubular connectors 55, 60. The first outer tubular connector 55 defines a first outer channel 56 extending between a first base end 57 attached to the second reservoir 70 and a first outer port 58. The first outer port 58 configured to connect to and/or fluidly communicate with the first receptacle port of the first inner tubular connector when attached thereto, without leaking. The first cleaning device portion 72a extends from the second reservoir 70 through and out of the first outer tubular connector 55 prior to the placement of the inner receptacle into the first chamber 51.

The second outer tubular connector 60 defines a second outer channel 61 extending between a second base end 62 attached to the second chamber 64 and a second outer port 63. The second outer port 63 is configured to connect to and/or fluidly communicate with the second receptacle port of the second inner tubular connector when attached thereto, without leaking. A second cleaning device portion 72b extends from the second chamber 64 through and out of the second outer tubular connector 60. In some embodiments, the second outer tubular connector is a septum positioned on and passing through inner base wall 54 to be configured to fluidly communicate the second chamber 64 with the second receptacle port of the inner receptacle when connected thereto, without leaking.

The second chamber 64 further includes a body portion 76 of an actuator 75 positioned therein and extending outwardly therefrom. The body portion 76 is connected to an actuator handle 77 positioned outside the second chamber 64. The actuator handle 77 is configured to be rotated or twisted to turn the body portion 76. Rotation or the turning of the body portion 76 causes the second cleaning device portion 72b attached thereto to be drawn from the first chamber 51 towards the second chamber 64. In some embodiments, the actuator handle is configured to turn in only one direction thereby ensuring proper use to draw the cleaning device towards the second chamber. In some embodiments, the outer base wall 53 may include a cut-out 69 configured to create sufficient space for the actuator handle 77 to rotate or twist without bumping into the outer base wall 53. The actuator may be manually operated or power operated.

Figure 6A:
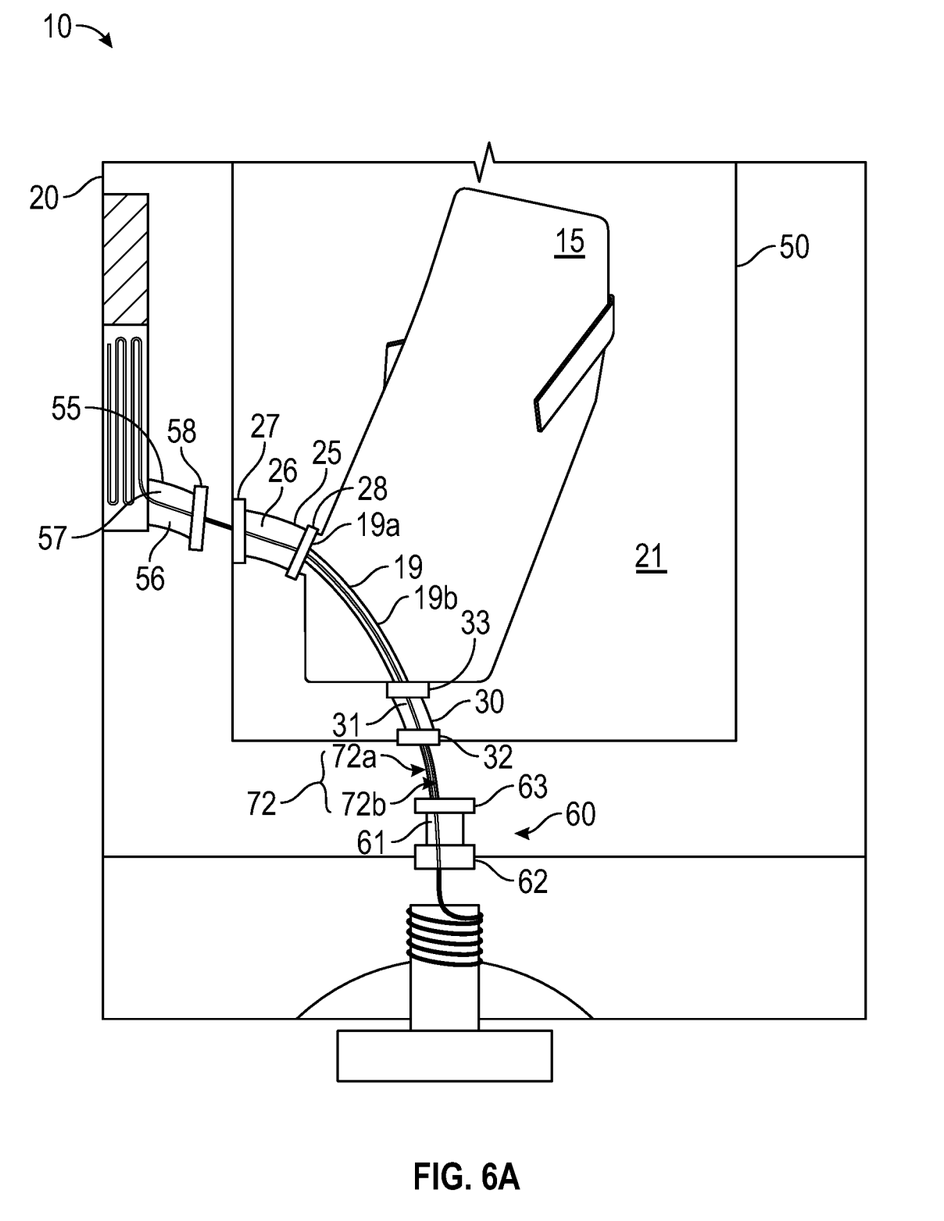
FIG. 6A-6D are schematic side views of a disposable cleaning unit including an inner and outer receptacle as described in at least embodiment herein.

FIGS. 6A-6D depict a schematic cross-sectional view of the disposable cleaning units 10, as well as methods of using the disposable cleaning units 10, wherein the inner receptacle 20 is combined with the outer receptacle 50 to clean the reusable medical device 15. In FIG. 6A, the medical device 15, such as an endoscope or bronchoscope, is positioned within the first cavity 21 of the inner receptacle 20 with the first and second openings 19a, 19b of the working channel 18 in fluid communication with the first and second inner tubular connectors 25, 30, respectively. In particular embodiments, the first and second device ports 28, 33 (of the first and second inner tubular connectors, respectively) are in fluid communication with the first and second openings 19a, 19b, respectively, of the working channel 18.

As further depicted in FIG. 6A, the first cleaning device portion 72a is fed through the first inner tubular connector 25, the working channel 18 and the second inner tubular connector 30 and joined and/or secured to the second cleaning device portion 72b in the first chamber 51 to form a single continuous cleaning device 72. The single cleaning device 72 extending between the first chamber 51 and the second chamber 64 or more particularly, between the second reservoir 70 of the first chamber 51 and the actuator body 76 of the second chamber 64. The first and second cleaning portions 72a, 72b can be joined using any suitable method including tying a knot, adhesives, Velcro, swaging, crimping, male/female connectors, barbs, threads, fasteners, and the like. In some embodiments, a free end of one of the first or second cleaning device portions may include a hook configuration while a free end of the other of the first or second cleaning device portions may include a loop configuration designed for receiving the hook configuration therein.

Figure 6B:
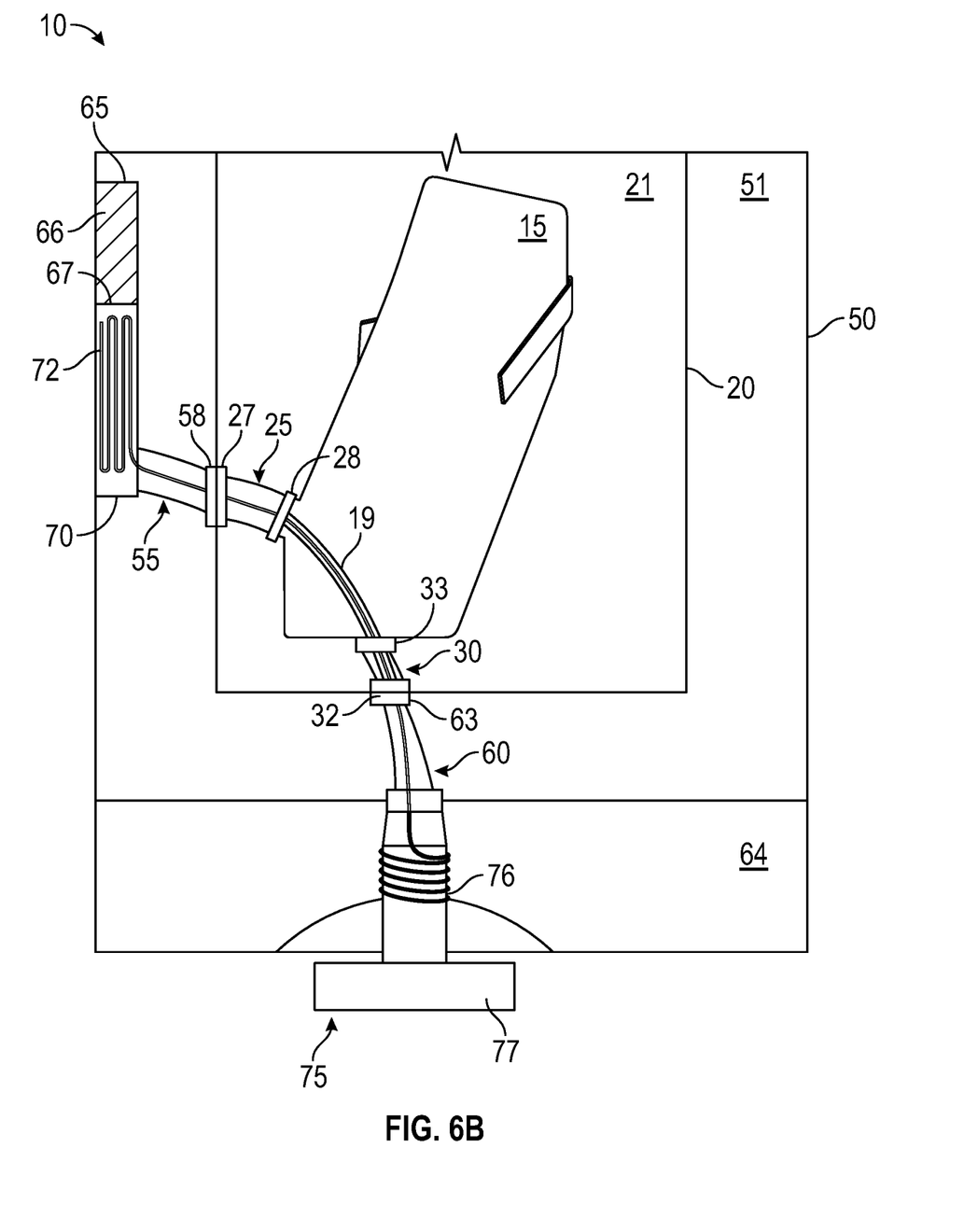

In FIG. 6B, following the attachment of the first and second cleaning device portions 72a, 72b to form one cleaning device 72, the first and second outer tubular connectors 55, 60 of the outer receptacle 50 may be placed in fluid communication with and/or connected to the first and second inner tubular connectors 25, 30 of the inner receptacle 20. More particularly, in some embodiments, the first outer port 58 of the first outer tubular connector 55 is connected to and/or placed in fluid communication with the first receptacle port 27 of the first inner tubular connector 25, and/or the second outer port 63 of the second outer tubular connector 60 is connected to and/or placed in fluid communication with the second receptacle port 32 of the second inner tubular connector 30. The second reservoir 70, the first outer tubular connector 55, the first inner tubular connector 25, the working channel 18, the second inner tubular connector 30, the second outer tubular connector 60 and the second chamber 64 are interconnected to each other and/or in fluid communication with each other, as shown in FIG. 6B.

Figure 6C:
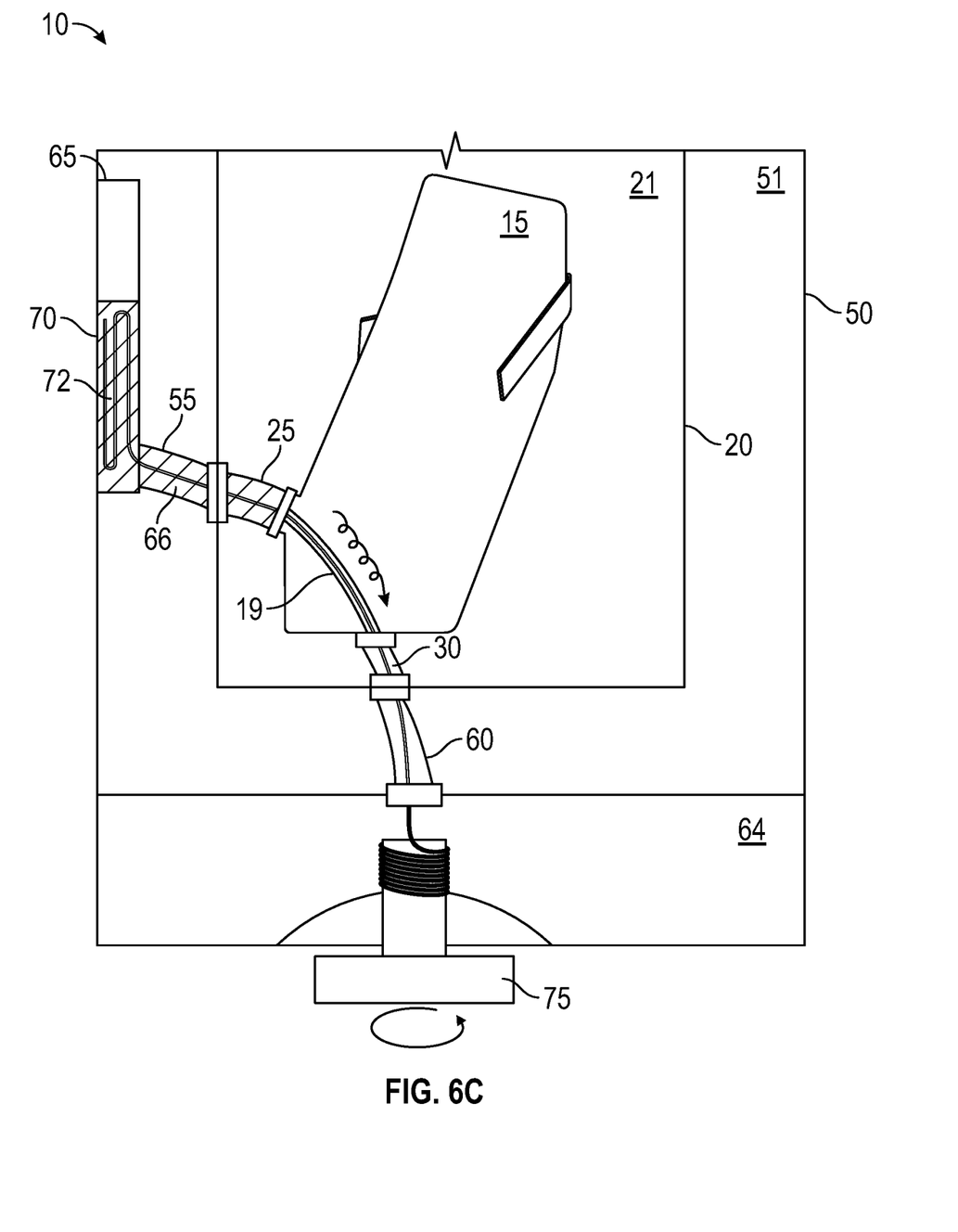

FIG. 6C depicts frangible member 67 in a ruptured or broken configuration allowing the cleaning fluid 66 to exit the first reservoir 65 and begin to enter the second reservoir 70 thereby coating portions of the cleaning device 72 still positioned within the second reservoir 70. In addition, because the second reservoir 70 is in fluid communication with various other connectors, ports, and/or openings, the cleaning fluid 66 may begin to leave the second reservoir 70 in a direction towards the second chamber 64.

As indicated by the arrow in FIG. 6C, the actuator 75 may be rotated or twisted to draw the cleaning device 72 from the second reservoir 70 towards the second chamber 64. As the actuator 75 is continued to be rotated, more of the cleaning device 72 will begin to wrap around the actuator body 76 and less of the cleaning device 72 will remain in the second reservoir 70. In addition, as the actuator 75 is rotated, the cleaning device 75 may also rotate about its longitudinal axis which will provide the cleaning device 72 with a scrubbing action both longitudinally as the cleaning device 72 is pulled through the working channel 18 but also radially as the cleaning device 72 is rotated inside the working channel 18. (as indicated by the spiral arrow).

Figure 6D:
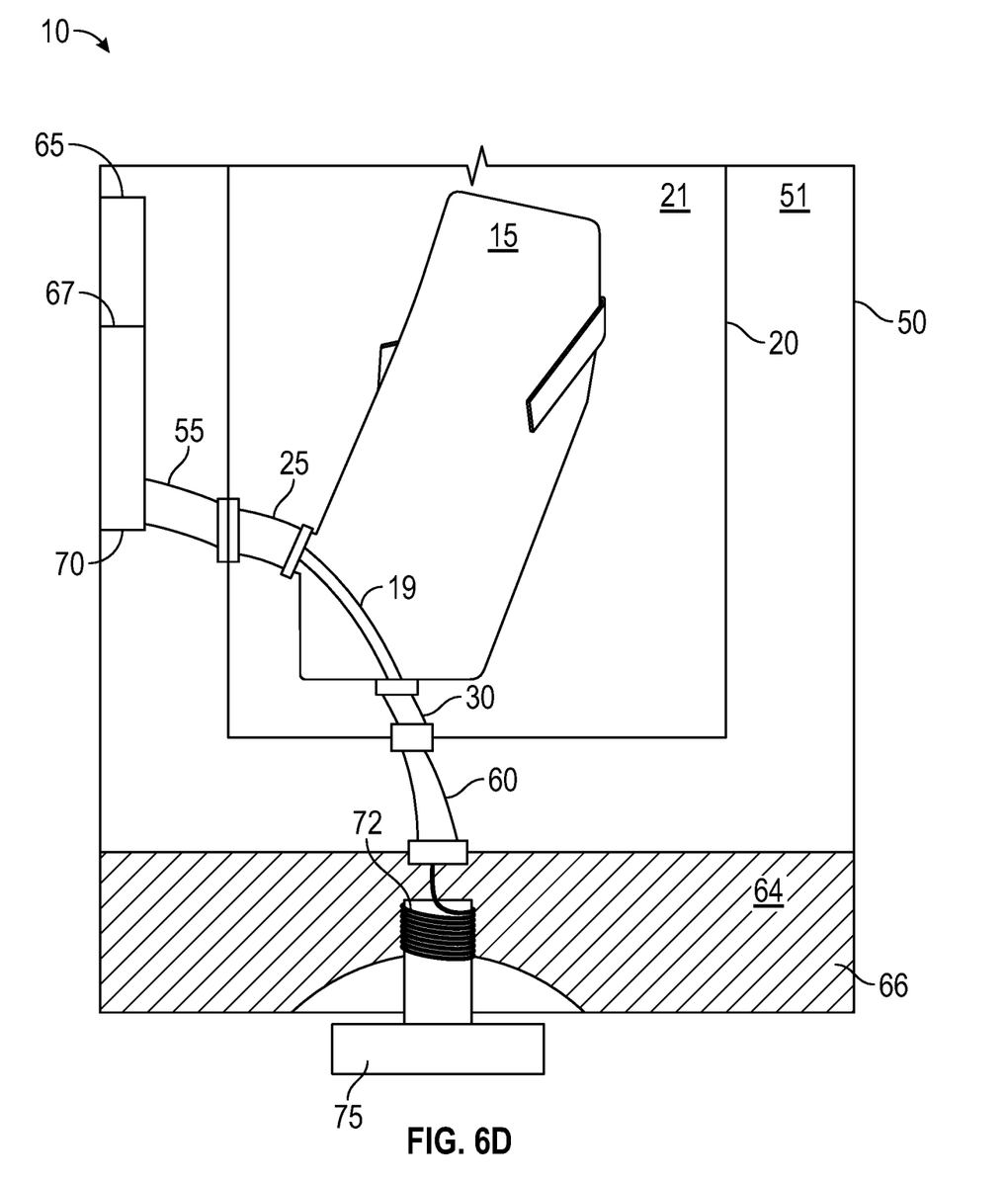

As shown in FIG. 6D, in some embodiments, the actuator 75 is rotated or twisted until the entire cleaning device 72 has passed through the working channel 18 of the medical device 15 and is positioned within the second chamber 64. As further shown in FIG. 6D, in some embodiments, the actuator 75 is rotated or twisted until all of the cleaning fluid 66 has passed through the working channel 18 of the medical device 15 and entered into the second chamber 64. Since the second chamber is sealed separately from the first chamber 51, the inner receptacle 20, and/or the medical device 15, recontamination of the working channel 18 with dirty fluids or a dirtied cleaning device is not possible. In addition, because each of the various connections between ports and/or openings are leak-proof, the cleaning fluid and the cleaning device are not exposed to exterior portions of the medical device and/or any internal components other than the working channel. Thus, the shelf life of the reusable medical is lengthened.

Figure 7A:
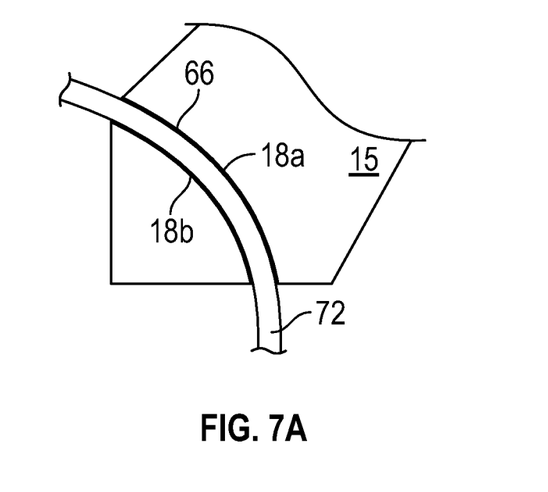
FIGS. 7A-7C are schematic side views of a cleaning device as described in at least one embodiment herein.
Figure 7B:
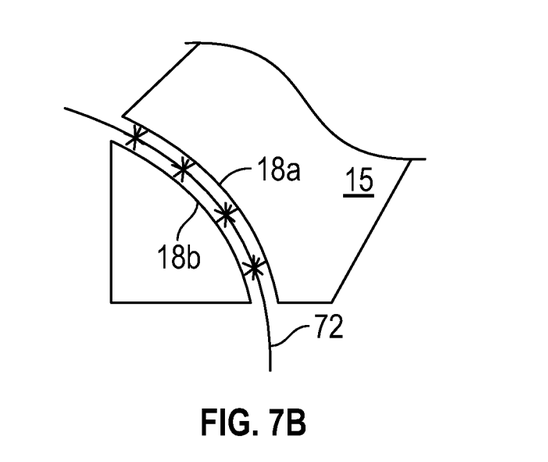
Figure 7C:
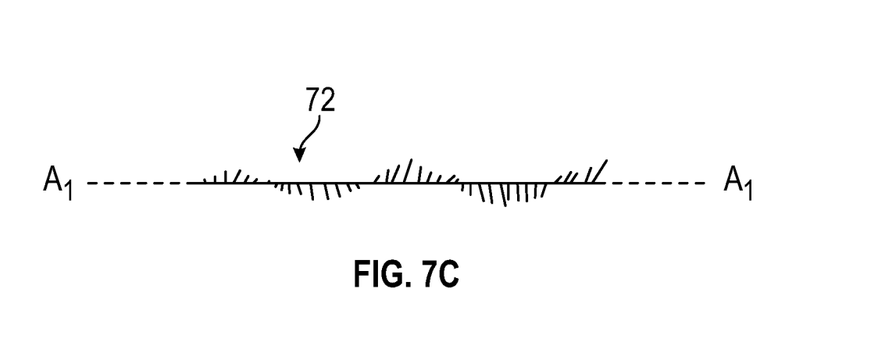

FIGS. 7A-7C depict schematic views of the cleaning device 72 described herein. The cleaning device 72 can be selected from a pipe cleaner or a brush. As shown specifically in FIG. 7A, in some embodiments, the cleaning device 72 may be a pipe cleaner having a thickness or diameter generally equal to or slightly larger than the thickness or diameter of the working channel 18. Such dimensions of the cleaning device 72 will ensure that when combined with the cleaning fluids inside the working channel 18 of the medical device 15, that one or both of the cleaning fluid or the cleaning device 72 comes into direct contact with the walls 18a, 18b of the working channel 18 thereby forcing any debris or dirt of the wall and out of the working channel 18 thereby cleaning the working channel 18. As shown specifically in FIGS. 7B and 7C, in some embodiments, the cleaning device 72 may be a brush including bristles configured either generally perpendicular to the longitudinal axis $A_1$ of the cleaning device (FIG. 7B) and/or in a spiral pattern rotating around the longitudinal axis of the cleaning device (FIG. 7C), the combination of the cleaning device and the cleaning fluids. Similarly, such dimensions of the cleaning device 72 will ensure that when combined with the cleaning fluids inside the working channel 18 of the medical device 15, that one or both of the cleaning fluid or the cleaning device 72 comes into direct contact with the walls 18a, 18b of the working channel 18 thereby forcing any debris or dirt of the wall 18a, 18b and out of the working channel 18 thereby cleaning the working channel 18.

In some embodiments, the disposable cleaning units described herein are particularly useful for cleaning bronchoscopes. In some embodiments, the cleaning units include a thermoform inner receptacle and an outer sealable pouch. In some embodiments, the outer pouch includes two sealable chambers and/or two chambers configured to be sealed. In some embodiments, the outer pouch includes a first chamber which can be sealed and unsealed on demand and a second chamber which is always sealed.

In some embodiments, the thermoform inner receptacle includes a first cavity, a first inner tubular connector, and a second inner tubular connector. The first cavity configured to receive a reusable bronchoscope therein, the reusable bronchoscope including a working channel defined therethrough, the working channel extending between a first opening and a second opening on the reusable bronchoscope. The first inner tubular connector defining a first inner channel extending between a first receptacle port and a first device port and a second inner tubular connector defining a second inner channel extending between a second receptacle port and a second device port, the first and second device ports configured to connect to the first and second openings, respectively, of the reusable bronchoscope.

In some embodiments, the outer sealable pouch includes a first and second chamber, and some combination of a first and second reservoir, and a first and second outer tubular connector. The first chamber being configured to receive the thermoform inner receptacle therein, with or without the medical device. The second includes at least a portion of an actuator connected to a second cleaning device portion of the cleaning device.

The first reservoir is configured to store a cleaning fluid and the second reservoir is configured to store at least a first portion of a cleaning device. Both are located within the first chamber.

The first outer tubular connector defines a first outer channel extending between a first base end attached to the second reservoir and a first outer port. The first outer port is configured to fluidly communicate with the first receptacle port of the first inner tubular connector when attached thereto, without leaking. The second outer tubular connector defines a second outer channel extending between a second base end attached to the second chamber and a second outer port. The second outer port is configured to fluidly communicate with the second receptacle port of the second inner tubular connector when attached thereto, without leaking.

Methods of cleaning a reusable medical device are also described herein, in some embodiments, a method of cleaning includes the following steps:

a) placing a first opening and a second opposite opening of a working channel defined within a reusable medical device in fluid communication with a first inner tubular connector and a second inner tubular connector of an inner receptacle configured to receive the reusable medical device;

b) positioning the inner receptacle including the reusable medical device in a first chamber of an outer receptacle, the first chamber further including a first reservoir including a cleaning fluid, a second reservoir including a first cleaning device portion, and first and second outer tubular connectors, the outer receptacle further including a second chamber including an actuator attached to a second cleaning device portion;

c) connecting the first cleaning device portion to the second cleaning device portion to form a cleaning device extending between the first and second chambers of the outer receptacle;

d) placing the first and second outer tubular connectors of the outer receptacle in fluid communication with the first and second inner tubular connectors, respectively, of the inner receptacle;

e) breaking a frangible member separating the first and second reservoirs to allow the cleaning fluid to pass through the first and second reservoirs; and f) activating the actuator positioned in the second chamber to draw the cleaning device from the second reservoir towards the second chamber.

In some embodiments, the step a) of the methods described herein may further include connecting a first device port of the first inner tubular connector to the first opening of the reusable medical device and connecting a second device port of the second inner tubular connector to the second opening of the reusable medical device.

In some embodiments, the step c) of the methods described herein may further include passing a first free end of the first cleaning device portion from the first outer tubular connector through the first inner tubular connector, the working channel, and the second inner tubular connector to meet a second free end of the second cleaning device portion and securing the first and second free ends to each other to form the cleaning device.

In some embodiments, the step d) of the methods described herein may further include connecting a first outer port of the first outer tubular connector to a first receptacle port of the first inner tubular connector and connecting a second outer port of the second outer tubular connector to a second receptable port of the second inner tubular connector.

In some embodiments, the step f) of the methods described herein may further include rotating the actuator in only direction until the entire cleaning device is positioned within the second chamber.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting but merely as exemplifications of particular embodiments. Those skilled in the art will envision other modifications within the scope and spirit of the claims appended hereto.

What is claimed is:

1. A disposable cleaning unit for a reusable medical device comprising:
   an inner receptacle including:
      a first cavity configured to receive a reusable medical device therein, the reusable medical device including a working channel defined therethrough, the working channel extending between a first opening and a second opening on the reusable medical device;
      a first inner tubular connector defining a first inner channel extending between a first receptacle port and a first device port; and
      a second inner tubular connector defining a second inner channel extending between a second receptacle port and a second device port, the first and second device ports configured to connect to the first and second openings, respectively, of the reusable medical device; and
   an outer receptacle including:
      a first chamber configured to receive the inner receptacle therein,
      a first reservoir configured to store a cleaning fluid,
      a second reservoir configured to store a first cleaning device portion of a cleaning device,
      a second chamber including at least a portion of an actuator connected to a second cleaning device portion of the cleaning device,
      a first outer tubular connector defining a first outer channel and extending between a first base end attached to the second reservoir and a first outer port, the first outer port configured to fluidly communicate with the first receptacle port of the first inner tubular connector when attached thereto, and a second outer tubular connector defining a second outer channel and extending between a second base end attached to the second chamber and a second outer port, the second outer port configured to fluidly communicate with the second receptacle port of the second inner tubular connector when attached thereto.

2. The disposable cleaning unit of claim 1, wherein the inner receptacle is a thermoform.

3. The disposable cleaning unit of claim 2, wherein the inner receptacle further comprises one or more sidewalls extending from a base wall defining the first cavity, and optionally including a cover opposite the base wall.

4. The disposable cleaning unit of claim 3, wherein at least a portion of the first tubular connector is defined within a first wall portion of the at least one sidewall and at least a portion of the second tubular connector is defined within a second wall portion of the at least one sidewall.

5. The disposable cleaning unit of claim 1, wherein the outer receptacle is a sealable pouch.

6. The disposable cleaning unit of claim 1, wherein the first portion of the cleaning device extends between a reservoir end and a first free end, the reservoir end stored within the second reservoir and the first free end extending through the first outer port of the first outer tubular connector.

7. The disposable cleaning unit of claim 6, wherein the second portion of the cleaning device extends between a chamber end and a second free end, the chamber end secured to the actuator in the second chamber and the second free end extending through the second outer port of the second outer tubular connector.

8. The disposable cleaning unit of claim 7, wherein the first end of the first portion of the cleaning device and the second free end of the second portion of the cleaning device are configured to lock to each other to form a single cleaning device extending from the first chamber of the outer receptacle, through the inner receptacle and the reusable medical device, to the second chamber of the outer receptacle.

9. The disposable cleaning unit of claim 1, wherein the cleaning fluid is selected from antiseptic liquids, antimicrobial liquids, antiviral liquids, sterile water, sterile saline, liquid detergents, and combination thereof.

10. The disposable cleaning unit of claim 1, wherein the cleaning device is selected from the group consisting of a pipe cleaner, a brush, and combinations thereof.

11. The disposable cleaning unit of claim 1, wherein at least one outer sidewall extending from an outer base wall and a supplemental base wall spaced from the outer base wall define the first and second chambers of the outer receptacle.

12. The disposable cleaning unit of claim 1, wherein the second reservoir is positioned beneath the first reservoir and separated by a frangible member configured to maintain separation of the cleaning fluid from the cleaning device until broken.

13. The disposable cleaning unit of claim 1, wherein the reusable medical device is an endoscope.

14. The disposable cleaning unit of claim 13, wherein the endoscope is a bronchoscope.

15. A disposable cleaning unit for a reusable bronchoscope comprising:
a thermoform inner receptacle including:
a first cavity configured to receive a reusable bronchoscope therein, the reusable bronchoscope including a working channel defined therethrough, the working channel extending between a first opening and a second opening on the reusable bronchoscope;
a first inner tubular connector defining a first inner channel extending between a first receptacle port and a first device port; and
a second inner tubular connector defining a second inner channel extending between a second receptacle port and a second device port, the first and second device ports configured to connect to the first and second openings, respectively, of the reusable bronchoscope; and
an outer pouch including:
a first chamber configured to receive the thermoform inner receptacle therein,
a first reservoir configured to store a cleaning fluid,
a second reservoir configured to store at least a first portion of a cleaning device,
a second chamber including at least a portion of an actuator connected to a second portion of the cleaning device,
a first outer tubular connector defining a first outer channel and extending between a first base end attached to the second reservoir and a first outer port, the first outer port configured to fluidly communicate with the first receptacle port of the first inner tubular connector when attached thereto,
a second outer tubular connector defining a second outer channel and extending between a second base end attached to the second chamber and a second outer port, the second outer port configured to fluidly communicate with the second receptacle port of the second inner tubular connector when attached thereto.

* * * * *